US009862761B2

(12) United States Patent
Brady et al.

(10) Patent No.: US 9,862,761 B2
(45) Date of Patent: *Jan. 9, 2018

(54) COMPOSITION AND METHOD FOR PREVENTING OR TREATING A TAUOPATHY

(71) Applicants: The Board of Trustees of the University of Illinois, Urbana, IL (US); Northwestern University, Evanston, IL (US)

(72) Inventors: Scott Thomas Brady, Chicago, IL (US); Lester I. Binder, Chicago, IL (US); Gerardo Andres Morfini, Chicago, IL (US); Nicholas M. Kanaan, Grand Rapids, MI (US); Nichole E. LaPointe, Santa Barbara, CA (US)

(73) Assignees: The Board of Trustes of the University of Illinois, Urbana, IL (US); Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/863,997

(22) Filed: Sep. 24, 2015

(65) Prior Publication Data
US 2016/0031978 A1  Feb. 4, 2016

Related U.S. Application Data

(63) Continuation of application No. 12/906,617, filed on Oct. 18, 2010, which is a continuation-in-part of application No. PCT/US2010/024893, filed on Feb. 22, 2010.

(60) Provisional application No. 61/279,102, filed on Oct. 16, 2009, provisional application No. 61/154,493, filed on Feb. 23, 2009.

(51) Int. Cl.
*C07K 16/18* (2006.01)
*A61K 39/395* (2006.01)
*C07K 14/47* (2006.01)
*G01N 33/50* (2006.01)
*A61K 38/00* (2006.01)

(52) U.S. Cl.
CPC .......... *C07K 16/18* (2013.01); *C07K 14/4711* (2013.01); *G01N 33/5058* (2013.01); *A61K 38/00* (2013.01); *A61K 39/3955* (2013.01); *C07K 2317/32* (2013.01); *C07K 2317/34* (2013.01); *C07K 2317/76* (2013.01); *G01N 2333/4709* (2013.01); *G01N 2333/912* (2013.01)

(58) Field of Classification Search
CPC ................ C07K 16/18; C07K 2317/34; C07K 2317/32; C07K 2317/76; C07K 2316/96
See application file for complete search history.

(56) References Cited

U.S. PATENT DOCUMENTS

| 5,811,310 A | 9/1998 | Ghanbari et al. ............. 436/518 |
| 2008/0050383 A1 | 2/2008 | Sigurdsson et al. ....... 424/141.1 |
| 2013/0028914 A1* | 1/2013 | Kayed .................... C07K 16/18 424/172.1 |

FOREIGN PATENT DOCUMENTS

WO  WO10/115843  10/2010

OTHER PUBLICATIONS

Bartos A et al. Patients with Alzheimer disease have elevated intrathecal synthesis of antibodies against tau protein and heavy neurofilament. J. Neuroimmunol. 252:100-105 (2012).*
Wencheng et al. Autoantibodies against tau, phosphorylated tau and PHF are produced in Alzheimer's disase and Down syndrome. Alzheimer's & Dementia, 2013, 9(4 Suppl):P365, Poster #P2-061.*
Amadoro et al. "Role of N-terminal Tau Domain Integrity on the Survival of Cerebellar Granule Neurons" Cell Death and Differentiation 2004 11(2):217-230.
Amadoro et al. "NMDA Receptor Mediates Tau-induced Neurotoxicity by Calpain and ERK/MAPK Activation" Proceedings of the National Academy of Sciences 103(8):2892-2897.
Andreadis, A. "Tau Gene Alternative Splicing: Expression Patterns, Regulation and Modulation of Function in Normal Brain and Neurodegenerative Diseases" Biochimica et Biophysica Acta 2005 1739(2-3):91-103.
Bellucci et al. "Abnormal Processing of tau in the Brain of Aged TgCRND8 Mice" Neurobiology of Disease 2007 27:328-338.
Berry et al. "Inhibition of Tau Polymerization by Its Carboxy-Terminal Caspase Cleavage Fragment" Biochemistry 2003 42(27):8325-8331.
Brandt et al. "Interaction of Tau with the Neural Plasma Membrane Mediated by Tau's Amino-terminal Projection Domain" The Journal of Cell Biology 1995 131(5):1327-1340.
Carmel et al. "The Structural Basis of Monoclonal Antibody Alz50's Selectivity for Alzheimer's Disease Pathology" The Journal of Biological Chemistry 1996 271(51):32789-32795.
Ebneth et al. "Overexpression of Tau Protein Inhibits Kinesin-dependent Trafficking of Vesicles, Mitochondria, and Endoplasmic Reticulum: Implications for Alzhimer's Disease" The Journal of Cell Biology 1998 143(3):777-794.
Gamblin et al. "Tau Polymerization: Role of Amino Terminus" Biochemistry 2003 42(7):2252-2257.
Gamblin et al. "Caspase Cleavage of Tau: Linking Amyloid and Neurofibrillary Tangles in Alzheimer's Disease" Proceedings of the National Academy of Sciences 2003 100(17):10032-10037.
GENBANK Accession No. NP_005901 GI: 6754638 "Microtubule-associated Protein Tau Isoform 2 [*Homo sapiens*]" May 1, 2011.

(Continued)

*Primary Examiner* — Kimberly A. Ballard
(74) *Attorney, Agent, or Firm* — Licata & Tyrrell P.C.

(57) ABSTRACT

The present invention is a composition and method for the prevention and treatment of a tauopathy. The composition of the invention includes N-terminal amino acid residues of the tau protein, which have been identified as being involved in toxic activation of a PP1/GSK3 signaling cascade and inhibition of fast axonal transport in human tauopathies.

7 Claims, 1 Drawing Sheet

(56) References Cited

OTHER PUBLICATIONS

Goedert et al. "Multiple Isoforms of Human Microtubule-Associated Protein Tau: Sequences and Localization in Neurofibrillary Tangles of Alzheimer's Disease" Neuron 1989 3(4):519-526.

Guillozet-Bongaarts et al. "Tau Truncation During Neurofibrillary Tangle Evolution in Alzheimer's Disease" Neurobiology of Aging 2005 26(7):1015-1022.

Gustke et al. "Domains of Tau Protein and Interactions with Microtubules" Biochemistry 1994 33(32):9511-9522.

Horowitz et al. "Early N-Terminal Changes and Caspase-6 Cleavage of Tau in Alzheimer's Disease" The Journal of Neuroscience 2004 24(36):7895-7902.

Jeganathan et al. "Global Hairpin Folding of Tau in Solution" Biochemistry 2006 45(7):2283-2293.

Lee et al. "Phosphorylation of Tau by Fyn: Implications for Alzheimer's Disease" The Journal of Neuroscience 2004 24(9):2304-2312.

Lee, G. "Tau and Src Family Tyrosine Kinases" Biochimica et Biophysica Acta 2005 1739(2-3):323-330.

Luo et al. "Novel Isoforms of Tau that Lack the Microtubule-binding Domain" Journal of Neurochemistry 2004 90(2):340-351.

Morfini et al. "Tau Binding to Microtubules Does Not Directly Affect Microtubule-Based Vesicle Motility" Journal of Neuroscience Research 2007 85(12):2620-2630.

Preuss et al. "The 'Jaws' Model of Tau-microtubule Interaction Examined in CHO Cells" Journal of Cell Science 1997 110(6):789-800.

Seitz et al. "Single-molecule Investigation of the Interference Between Kinesin, Tau and MAP2c" The EMBO Journal 2002 21(18):4896-4905.

Vershinin et al. "Multiple-motor Based Transport and Its Regulation by Tau" 2007 104(1):87-92.

Yuan et al. "Axonal Transport Rates In Vivo Are Unaffected by Tau Deletion or Overexpression in Mice" The Journal of Neuroscience 2008 28(7):1682-1687.

Office Communication dated Jul. 21, 2011 in U.S. Appl. No. 12/906,617, filed Oct. 18, 2010.

Office Communication dated May 11, 2012 in U.S. Appl. No. 12/906,617, filed Oct. 18, 2010.

Office Communication dated Apr. 11, 2013 in U.S. Appl. No. 12/906,617, filed Oct. 18, 2010.

Office Communication dated Oct. 9, 2014 in U.S. Appl. No. 12/906,617, filed Oct. 18, 2010.

Office Communication dated May 8, 2015 in U.S. Appl. No. 12/906,617, filed Oct. 18, 2010.

\* cited by examiner

SEQUENCE LISTING

<160> NUMBER OF SEQ ID NOS: 8

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide

<400> SEQUENCE: 1

Ala Glu Pro Arg Gln Glu Phe Glu Val Met Glu Asp His Ala Gly Thr
1               5                   10                  15

Tyr

<210> SEQ ID NO 2
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 2
gggagtgcct ggggagccgg gctcgctgta gccgctgcg                                 39

<210> SEQ ID NO 3

```
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 3
cgcagcggct acagcgagcc cggcgaacca ggcactccc                      39

<210> SEQ ID NO 4
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 4
gagcccggcg aaccaggcga acccggcagc cgctc                          35

<210> SEQ ID NO 5
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 5
gacaaaaaag ccaaggatat cggggctgat gg                             32

<210> SEQ ID NO 6
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 6
ggaggcggga aggatatcgt gcagataatt aataagaagc                     40

<210> SEQ ID NO 7
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 7
ggactggaag cgatgacaaa aaagccaagg tgcagataat taataagaag c        51

<210> SEQ ID NO 8
<211> LENGTH: 13
<212> TYPE: PRT
<213> ORGANISM: Artificial sequence
<220> FEATURE:
<223> OTHER INFORMATION: Synthetic peptide

<400> SEQUENCE: 8

Lys Arg Arg Glu Ile Leu Ser Arg Arg Pro Ser Tyr Arg
1               5                   10
```

COMPOSITION AND METHOD FOR PREVENTING OR TREATING A TAUOPATHY

INTRODUCTION

This application is a continuation application of U.S. Ser. No. 12/906,617 filed Oct. 18, 2010, which claims benefit of priority to U.S. Provisional Application Ser. No. 61/279,102 filed Oct. 16, 2009 and which is a continuation-in-part application of PCT/US2010/024893 filed Feb. 22, 2010, which claims benefit of priority to U.S. Provisional Application Ser. No. 61/154,493, filed Feb. 23, 2009, the contents of each of which are incorporated herein by reference in their entireties.

This invention was made with government support under contract numbers NS049834 and AG14453 awarded by the National Institutes of Health and contract numbers NS23868, NS23320, NS41170, and NS43408 awarded by the National Institute of Neurological Disorders and Stroke. The government has certain rights in the invention.

BACKGROUND OF THE INVENTION

Tau is a microtubule-associated protein (MAP) involved in microtubule dynamics and maintenance (Amos & Schlieper (2005) Adv. Protein Chem. 71:257-298), and insoluble filamentous tau aggregates form in Alzheimer's disease (AD) and several other neurodegenerative tauopathies (Gamblin et al. (2003) Biochemistry 42:15009-15017). Despite the strong positive correlation between the appearance of filamentous tau and neuronal dysfunction (Binder et al. (2005) Biochim. Biophys. Acta 1739:216-223), no toxic mechanism has been directly tied to these structures, and as a result the molecular basis of tau filament toxicity remains a subject of debate (King (2005) Biochim. Biophys. Acta 1739:260-267).

In AD, degenerating neurons exhibit alterations in synaptic function (Bell, et al. (2006) Eur. J. Pharmacol. 545: 11-21; Yoshiyama, et al. (2007) Neuron 53:337-351), the appearance of neuritic varicosities, and the mislocalization of various membrane-bound organelles (MBOs), all of which indicate that intracellular transport is disrupted in this disease (Morfini, et al. (2002) Neuromol. Med. 2:89-99) (Morfini, et al. (2009) J. Neurosci. 29(41):12776-86). Given these observations, and the central role of tau in AD pathology, the effects of monomeric tau on microtubule-dependent fast axonal transport (FAT) has been investigated. Reports have been published arguing that supraphysiological levels of soluble tau can reduce anterograde FAT by interfering with the attachment of the molecular motor kinesin (Ebneth, et al. (1998) J. Cell Biol. 143:777-794; Seitz, et al. (2002) EMBO J. 21:4896-4905; Vershinin, et al. (2007) Proc. Natl. Acad. Sci. USA 104:87-92). However, there is no evidence that such levels of tau are seen in normal or pathological neurons. Further, functional experiments in isolated squid axoplasm (Morfini, et al. (2007) J. Neurosci. Res. 85(12): 2620-30) and mice (Yuan, et al. (2008) J. Neurosci. 28(7): 1682-7) do not support such an idea. Remarkably, even though the hallmark of AD and other tauopathies is the presence of intracellular tau filaments, the biological effects of filamentous tau on FAT have not been assessed.

SUMMARY OF THE INVENTION

The present invention is a composition composed of a tau peptide of SEQ ID NO:1, or fragment thereof, in admixture with a pharmaceutically acceptable carrier. In one embodiment, the peptide or fragment includes a post-translational modification such as a nitro group or a phosphate group.

The invention also features a method for using the composition of the invention in the prevention or treatment of a human tauopathy including Alzheimer's disease. This method involves administering to a subject in need thereof an effective amount of a composition containing a tau peptide of SEQ ID NO:1, a tau peptide fragment or tau peptide binding agent, so that the tauopathy is prevented or treated.

A method for the identification of agents to treat a tauopathy is also provided. This method includes the steps of contacting a test cell with a test agent in the presence of a tau peptide of SEQ ID NO:1 that activates PP1 and GSK3 and inhibits anterograde fast axonal transport; and determining whether the test agent restores PP1 and GSK3 activity and prevents anterograde fast axonal transport inhibition in the cell treated with a tau peptide of SEQ ID NO:1, thereby identifying an agent for treating a tauopathy.

BRIEF DESCRIPTION OF THE DRAWINGS

FIG. 1A shows FAT in the presence of Tau ht40 filaments (2 µM) and the TNT1 antibody. FIG. 1B shows inhibition of FAT by Tau ht40 filaments (2 µM).

DETAILED DESCRIPTION OF THE INVENTION

Figure 1A:
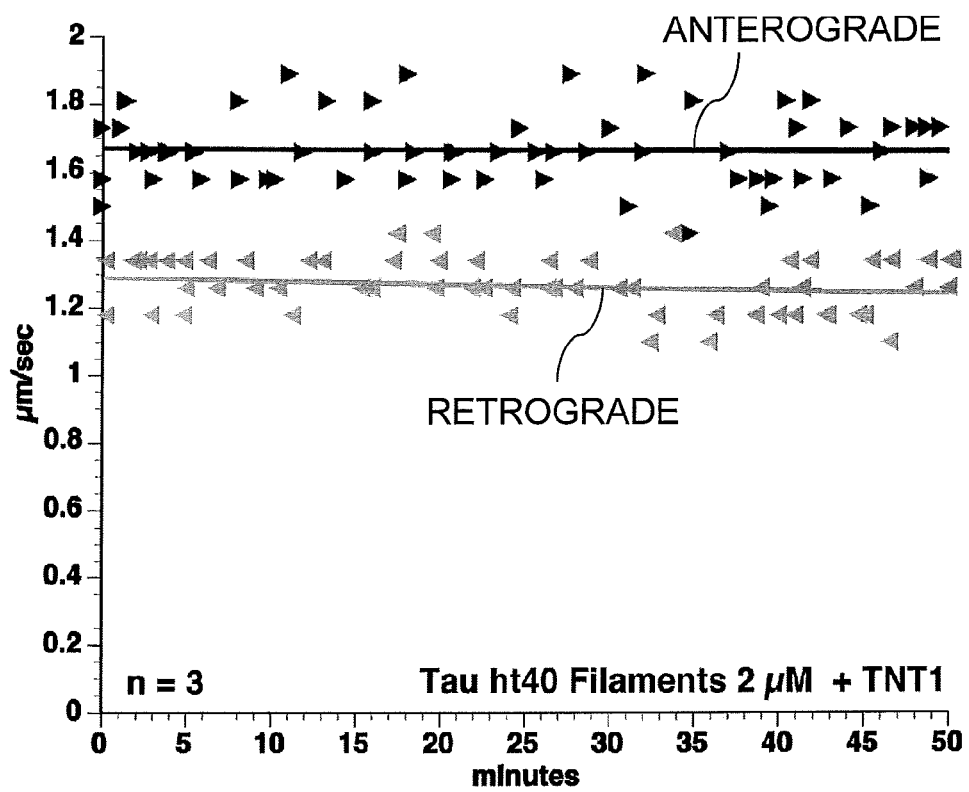
FIG. 1A and FIG. 1B show that an anti-PAD antibody can block the ability of tau filaments to activate PP1/GSK3 signaling and inhibit FAT.

Tau is a microtubule-associated protein that forms the fibrillar inclusions in Alzheimer's disease (AD) and other tauopathies. It has now been demonstrated that tau filaments inhibit anterograde fast axonal transport (FAT) via an N-terminal-dependent activation of a protein phosphatase 1 (PP1)-glycogen synthase (GSK)-3 signaling cascade; however, soluble tau does not affect FAT. The role of tau conformation was determined in axonal transport inhibition using conformation incompetent N-terminal isoforms of tau (6D and 6P), a synthetic peptide of amino acids 2-18 in tau, and tau with disease-associated modifications that impair global tau folding. The results indicated that 6D tau and a peptide encompassing amino acids 2-18 of tau, referred to herein as the "phosphatase-activating domain" (PAD), inhibit anterograde FAT via the PP1-GSK3 cascade in isolated squid axoplasm. Moreover, soluble monomers of tau pseudophosphorylated at the AT8 site (S199/S202/T205) associated with tau hyperphosphorylation in AD, and a deletion mutant of tau (deletion of amino acid residues 144-273) found in a form of familial frontotemporal dementia inhibit anterograde FAT. These results demonstrate that exposure of the PAD in tau is critical to initiating the PP1-GSK3 pathway leading to inhibition of anterograde FAT, and that disease-associated modifications or mutations in tau that increase exposure of the PAD via effects on tau folding can cause a toxic gain-of-function in soluble tau.

The results herein indicate that the PAD peptide sequence in human tau is both necessary and sufficient for inhibition of conventional kinesin-mediated anterograde fast axonal transport through a mechanism involving activation of protein phosphatase 1 (PP1). Accordingly, synthetic PAD peptides find use as an antigen for immunotherapy approaches for the treatment of tauopathies, as well as a basis in high high-throughput screening assays for drugs useful in the treatment of tauopathies and Alzheimer's disease. In addition, this peptide provides a basis for devising therapeutic strategies based on modification of the PAD peptide sequence in endogenous tau including phosphorylation of Thr17 or Tyr18 or nitration of Tyr18.

Accordingly, the present invention is a composition containing a tau peptide encompassing the sequence Ala-Glu-Pro-Arg-Gln-Glu-Phe-Glu-Val-Met-Glu-Asp-His-Ala-Gly-Thr-Tyr (SEQ ID NO:1) present in human tau or a fragment thereof. A tau peptide or tau peptide fragment of the present invention is intended to include a peptide containing between 5 and 20 amino acid residues. In particular, the tau peptide of the invention is 5, 6, 7, 8, 9, 10, 11, 12, 13, 14, 15, 16, or 17 amino acid residues in length. In one embodiment, the tau peptide of the invention comprises SEQ ID NO:1. In another embodiment, the tau peptide of the invention consists of SEQ ID NO:1. In a further embodiment, a tau peptide fragment is a peptide composed of between 5 to 16 amino acid residues of the sequence set forth in SEQ ID NO:1.

The tau peptide of the invention can be composed of naturally occurring amino acids, or contain one or more non-naturally occurring amino acids. The non-naturally occurring amino acids may be L-, dextrorotatory (D), or mixtures thereof. Non-naturally occurring amino acids are those amino acids that typically are not synthesized in normal metabolic processes in living organisms, and do not naturally occur in proteins. The non-naturally occurring amino acid can be present at any position in the peptide. For example, the non-naturally occurring amino acid can be at the N-terminus, the C-terminus, or at any position between the N-terminus and the C-terminus. The non-natural amino acids may, for example, include alkyl, aryl, or alkylaryl groups. Some examples of alkyl amino acids include α-aminobutyric acid, β-aminobutyric acid, and γ-aminobutyric acid. Some examples of aryl amino acids include ortho-, meta-, and para-aminobenzoic acid. Some examples of alkylaryl amino acids include ortho-, meta-, and para-aminophenyleacetic acid, and γ-phenyl-β-aminobutyric acid.

In one embodiment, the tau peptide or fragment is post-translationally modified. Such post-translational modifications are well-known in the art and include, but are not limited to, phosphorylation, acylation, acetylation, alkylation, amidation, glycosylation, nitrosylation, nitration, methylation, myristoylation, oxidation and the like. In particular embodiment, a phosphate or nitro group is incorporated into the peptide or peptide fragment. Moreover, to facilitate purification, the peptide or peptide fragment can be prepared with a tag, e.g., a his6 or FLAG tag of use in affinity purification.

Tau peptides and tau peptide fragments can be produced by any suitable method including recombinant protein production or chemical synthesis, or a combination thereof, all of which are routinely used in the art. Where the tau peptide or tau peptide fragment is prepared without a tag attached, any well-known procedures for purification can be used. Such procedures include, without limitation, ion exchange chromatography, hydroxyapatite chromatography, hydrophobic interaction chromatography, molecular sieve chromatography, HPLC, and native gel electrophoresis in combination with gel elution. In some cases, two or more of these techniques may be combined to achieve increased purity. In particular embodiments, the tau peptide or tau peptide fragment is isolated and purified, e.g., to greater than 90%, 95%, 97%, 98%, or 99% homogeneity.

For therapeutic use, particular embodiments include the tau peptide or tau peptide fragment in admixture with a pharmaceutically acceptable carrier. The carrier material may be water, preferably supplemented with other materials common in solutions for administration to mammals. Typically, a tau peptide or tau peptide fragment for therapeutic use will be administered in the form of a composition containing purified tau peptide or tau peptide fragment in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Compositions of the invention can contain buffers known to those having ordinary skill in the art with an appropriate range of pH values, including Tris buffer of about pH 7.0-8.5, or acetate buffer of about pH 4.0-5.5, which may further include sorbitol or a suitable substitute thereof.

The tau peptide or tau peptide fragment can be administered alone, in admixture with a carrier, or conjugated to a carrier, or alternatively in combination with a conventional immunostimulatory adjuvant to boost the host immune response. The tau peptide or tau peptide fragment can be administered intramuscularly, orally, intravenously, intraperitoneally, intracerebrally (intraparenchymally), intracerebroventricularly, intratumorally, intralesionally, intradermally, intrathecally, intranasally, intraocularly, intraarterially, topically, transdermally, via an aerosol, infusion, bolus injection, implantation device, sustained release system etc. Alternatively, the tau peptide or tau peptide fragment can be expressed in vivo by administering a gene that expresses the tau peptide or tau peptide fragment, by administering a vaccine that induces such production or by introducing cells, bacteria or viruses that express the peptide in vivo, either because of genetic modification or otherwise.

In addition to a tau peptide or tau peptide fragment, the present invention also includes binding agents, e.g., an antibody or aptamer, that specifically bind the instant tau peptide and block the toxic effects of tau. By way of illustration, antibodies specific for the PAD peptide were generated. One of these antibodies, TNT1, was characterized and shown to recognize denatured tau or tau from the brains of Alzheimer's patients, but not wild-type soluble monomer. Immunoctyochemistry with TNT1 on control and AD brains indicated that it was an early marker for AD and Mild Cognitive Impairment (MCI), which is thought to be an early stage of AD pathology. In addition, the TNT1 antibody was shown to prevent the inhibition of FAT in isolated axoplasm due to tau filaments.

Tau binding agents can be produced by any suitable conventional method. For example, wherein the tau binding agent is an antibody, the instant tau peptide is used to immunize, e.g., a mouse or rabbit, and monoclonal or polyclonal antibodies are generated by routine protocols. Fragments of such antibodies can also be generated and used as tau peptide binding agents. As with the tau peptide or tau peptide fragment, a tau peptide binding agent finds use in immunotherapy approaches for the treatment of tauopathies. In this respect, the tau binding agent, e.g., an exogenous intrabody or antibody fragment delivered via gene therapy techniques, selectively binds tau filaments and prevents the inhibition of FAT by the tau filaments.

To inhibit, block, or attenuate the toxic effects of tau, the present invention also includes the use of a tau peptide, tau peptide fragment or tau peptide binding agent as disclosed herein in an immunological method for preventing or treating a tauopathy. As used herein, a tauopathy is a group of neurodegenerative diseases characterized by accumulation of filamentous, insoluble tau (i) protein in the brain. As is known in the art, tauopathies include Alzheimer's disease, progressive supranuclear palsy, frontotemporal dementias, Pick's disease, corticobasal degeneration, post-encephalitic parkinsonism and other related disorders.

Treatment in accordance with the present invention includes administering to a subject in need of treatment, i.e., a subject with a tauopathy or at risk of a tauopathy (e.g., a subject with a family history of a tauopathy or exhibiting one or more signs or symptoms of a tauopathy), an immunotherapy-related composition containing an effective amount of a tau peptide, tau peptide fragment, or tau binding agent so that one or more signs or symptoms of the tauopathy are ameliorated, delayed or prevented. In particular embodiments, treatment results in the restoration of PP1 and GSK3 activities to their normal levels; and/or the restoration of fast axonal transport and neuron function; as compared to a subject not receiving such treatment. In this respect, clinical efficacy can be determined by monitoring or detecting levels of fast axonal transport or signal transduction of the PP1-GSK3 pathway in the subject being treated with the tau peptide or tau peptide fragment.

Subjects benefiting from such treatment include humans as well as other animals that develop tauopathies. In this context, a subject is understood to include any mammalian species in which treatment of a tauopathy is desirable, including agricultural and domestic mammalian species, as well as humans. Dosing of the peptide or peptide fragment of the invention can be based upon initial studies in an animal model of a tauopathy and subsequent clinical trials routinely carried out in the art.

Having identified the specific mechanism of tau-mediated inhibition of anterograde fast axonal transport and neuronal dysfunction in tauopathies, the tau peptide or tau peptide fragment disclosed herein is of particular use in identifying agents that target this mechanism. In this respect, the present invention also features a method for identifying an agent for treating a tauopathy. In accordance with this method, a test cell is contacted with a test agent in the presence of a tau peptide of SEQ ID NO:1 that activates the PP1 and GSK3 signaling cascade and inhibits anterograde fast axonal transport; and it is subsequently determined whether the test agent preserves or restores PP1 and/or GSK3 activities and/or prevents anterograde fast axonal transport inhibition in the cell. In this respect, the test agent can be added to the cell before or after the tau peptide or tau peptide fragment.

Cells of use in the instant method include primary neurons, as well as neuronal progenitor cells and neuron cells from a model system (e.g., an animal model or a neuronal cell line) or other cell lines with suitable properties (e.g., non-neuronal cells that have been engineered to express pathogenic tau and express one or more of PP1, GSK3, and kinesin). In this regard, by exposing cells to the pathological tau peptide or tau peptide fragment, the cells exhibit pathological signs of a tauopathy including activation of the PP1-GSK3 signaling cascade and inhibition of anterograde fast axonal transport. Exposure of cells to a tau peptide or tau peptide fragment can be achieved by recombinant expression of exogenous tau peptide or tau peptide fragment by the cells, endogenous expression of the tau peptide or tau peptide fragment, or injection or contact of cells with the tau peptide or tau peptide fragment. Such methods of exposing cells to peptides or peptide fragments are routinely practiced in the art and any suitable method can be employed. In some embodiments, cells of the present invention are isolated (e.g., grown in vitro). In other embodiments, cells of the instant method are in vivo.

Test agents encompass numerous chemical classes, although typically they are organic compounds. In some embodiments, the candidate agents are small organic compounds, i.e., those having a molecular weight of more than 50 yet less than about 2500, preferably less than about 1000 and, more preferably, less than about 500. Candidate test agents generally include functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The candidate test agents can have a cyclic carbon or heterocyclic structure and/or aromatic or polyaromatic structures substituted with one or more of the above-identified functional groups. Candidate test agents also can be biomolecules such as peptides, proteins, antibodies, saccharides, fatty acids, sterols, isoprenoids, purines, pyrimidines, derivatives or structural analogs of the above, or combinations thereof and the like.

Restoration of suitable PP1/GSK3 activities and preservation of fast axonal transport in a cell finds application in research focusing on mechanisms of fast axonal transport and pathological tau protein activity as well as in the amelioration, delay, or prevention of tauopathies as described herein.

The invention is described in greater detail by the following non-limiting examples.

Example 1: Materials and Methods

Reagents.

CREBpp was synthesized and purified (95%) by New England Peptide (Gardner, Mass.). Inhibitor-2 (I-2), 5B203580, and okadaic acid (OK) were purchased from Calbiochem (San Diego, Calif.). Arachidonic acid (AA; Cayman Chemical, Ann Arbor, Mich.) was stored at −20° C., and working solutions were prepared in 100% ethanol immediately prior to use. Mammalian protease inhibitor cocktail was from Sigma (St. Louis, Mo.). Active fyn kinase was purchased from Millipore, and horse anti-mouse and goat anti-rabbit antibodies from Vector Labs. ING-135 was synthesized as described previously (Kozikowski, et al. (2007) *J. Am. Chem. Soc.* 129:8328-8332). The 9G3 antibody is known in the art (Lee, et al. (2004) *J. Neurosci.* 24:2304-2312) as is the R1 tau antibody (Berry, et al. (2004) *J. Neurocytol.* 33(3):287-95). Amino acid 2-18 peptide and scrambled 2-18 peptide (both >98% purity) were synthesized (GenScript, Piscataway, N.J.).

Recombinant Proteins.

The full-length tau used in this study (hTau40) corresponded to the longest isoform in adult human brain, containing 441 amino acids and four microtubule-binding repeats (MTBRs) (Goedert, et al. (1989) *Neuron* 3(4):519-26; GENBANK Accession No. NP_005901). K23 was a tau construct lacking both alternatively spliced N-terminal exons and all four MTBRs. Tau6D and Tau6P were tau isoforms lacking the MTBR region and the C-terminus of canonical tau. The alternative splicing that generated these isoforms occurred in exon 6 and introduces a unique 11 amino acid residue sequence followed by a stop codon. The specific 11 amino acid residues vary depending on whether the splice site is proximal or distal to the beginning of exon 6 (Luo, et al. (2004) *J. Neurochem.* 90:340-351). Tau6D and Tau6P isoforms were generated by restriction digestion and ligation of constructs previously described (Luo, et al. (2004) supra) and from hTau40-encoding constructs (Gustke, et al. (1994) *Biochemistry* 33:9511-9522; Carmel, et al. (1996) *J. Biol. Chem.* 271:32789-32795). All other constructs used in this study are known in the art: 42-18 (Gamblin, et al. (2003) Biochemistry 42:2252-2257), 1-421 (Gamblin, et al. (2003) Proc. Natl. Acad. Sci. USA 100: 10032-10037), K23 (Preuss, et al. (1997) J. Cell Sci. 110: 789-800). All proteins were expressed in *Escherichia coli* and purified by means of an N-terminal poly-histidine tag (Carmel, et al. (1996) supra; Abraha, et al. (2000) J. Cell Sci. 113:3737-3745).

Site-directed mutagenesis (Stratagene, QUICKCHANGE II Kit) was used to create point mutations in full-length tau constructs. Serine 199, Ser202, and Thr205 were mutated to glutamic acid (Glu) to create the AT8 pseudophosphorylated mutant protein (AT8 tau). Deletion of amino acids 144-273 (Δ144-273 tau) was created by inserting EcoRV restriction sites flanking the appropriate region of the cDNA. Following EcoRV digestion and T4 ligation (New England Biolabs; according to manufacturer's instructions), the remaining EcoRV site was removed via deletion using the site-directed mutagenesis kit. The primers used for the generation of AT8 and Δ144-273 tau cDNAs are listed in Table 1. The tau cDNA plasmid constructs were amplified in XL-1 blue supercompetent *E. coli*, purified with the QIAGEN Miniprep kit, and cDNA sequences were verified by DNA sequencing. T7 express supercompetent *E. coli* cells were used to express tau constructs and the proteins were purified through his-tag high affinity resin and size exclusion chromatography (Carmel, et al. (1996) supra).

TABLE 1

| Construct | Primer Sequence (5'→3') | SEQ ID NO: |
|---|---|---|
| S199E | GGG AGT GCC TGG GGA GCC GGG CTC GCT GTA GCC GCT GCG | 2 |
| S199E/S202E | CGC AGC GGC TAC AGC GAG CCC GGC GAA CCA GGC ACT CCC | 3 |
| S199E/S202E/ T205E | GAG CCC GGC GAA CCA GGC GAA CCC GGC AGC CGC TC | 4 |
| N-terminal EcoRV | GAC AAA AAA GCC AAG GAT ATC GGG GCT GAT GG | 5 |
| C-terminal EcoRV | GGA GGC GGG AAG GAT ATC GTG CAG ATA ATT AAT AAG AAG C | 6 |
| EcoRV Deletion | GGA CTG GAA GCG ATG ACA AAA AAG CCA AGG TGC AGA TAA TTA ATA AGA AGC | 7 |

Immunoblots.

Samples were heated to 60° C. for 5 minutes and separated on 10% acrylamide gels via SDS-PAGE. The proteins were transferred to nitrocellulose membranes, blocked in 2% non-fat dry milk Tris-buffered saline (NFDM-TBS; Tris 50 mM, NaCl 150 mM, pH 7.4). The membranes were incubated in primary antibodies (R1-1:300,000 and 9G3-1: 8000) overnight at 4° C. The next day, the membranes were rinsed in TBS+0.1% TWEEN 20 and then incubated in the appropriate secondary antibody (1:5000; diluted in 2% NFDM-TBS). Immunoreactivity was visualized using ECL solution and the level of reactivity was quantified by measuring the optical density of immunoreactive bands with ImageJ software (v1.41, NIH). The average pixel intensities of the main tau bands were measured. Data are expressed as the ratio of 9G3 intensity to R1 intensity (error bars— s.e.m.).

Dot Blots.

Tau constructs were spotted onto nitrocellulose membranes (1 ng/μl, 1 μl per spot), blocked with 5% nonfat dry milk in Tris-buffered saline, pH 7.4, and probed with the monoclonal antibodies Tau12 (2 ng/ml), Tau5 (20 ng/ml), and Tau46.1 (20 ng/ml), which recognize amino acid residues 9-18, 210-230, and 428-441, respectively (Kosik, et al. (1988) *Neuron* 1:817-825; Carmel, et al. (1996) supra; Ghoshal, et al. (2002) *Exp. Neurol.* 177:475-493). Primary antibody binding was detected with HRP-conjugated anti-mouse secondary antibody (Vector Laboratories, Burlingame, Calif.) and ECL developing solution (GE Healthcare, Amersham, United Kingdom).

Microtubule-Binding Assays.

Squid optic lobes were dissected and flash frozen in liquid nitrogen (Morfini, et al. (2007) supra). One and one-half grams of freshly thawed squid optic lobes was homogenized in 2.5 ml of BRB80 buffer (80 mM PIPES, 1 mM $MgCl_2$, and 1 mM EGTA) and 1/100 mammalian protease inhibitor cocktail (Sigma), plus phosphatase and kinase inhibitors (Calbiochem) as follows: 1/200 phosphatase inhibitor cocktail II, 200 mM sodium orthovanadate, 200 nM mycrocystin RR, 50 nM okadaic acid, 100 nM K252a, 100 nM staurosporine. Squid optic lobe homogenate was prepared at 4° C. using a glass Dounce homogenizer. This homogenate was centrifuged at 12,500 g for 20 minutes at 4° C. The supernatant fraction was transferred to a new tube and centrifuged at 125,000 g for 5 minutes at 4° C. in a TL100.3 rotor (Beckman, Fullerton, Calif.). The supernatant (cytosol) was transferred to a new tube, adjusted to 20 μM taxol, and incubated at 37° C. for 15 minutes to allow for microtubule polymerization. After this step, 200-μl aliquots of microtubule-containing cytosol were incubated alone or with htau40 or K23 tau constructs (5 μM final concentration) for 20 minutes at 37° C. Samples were loaded on top of a 60 μl BRB80 buffer plus 20% sucrose cushion and 20 μM taxol using 1.5-ml microcentrifuge tubes, and centrifuged for 5 minutes at 125,000 g at 4° C. using a TLA100.3 rotor (Beckman). Microtubule pellets were resuspended in 200 μl of BRB80. Pellets and supernatant fractions were adjusted to 1× gel loading buffer (GLB) using a 5×GLB stock (0.35 M Tris-HCl, pH 6.8, 10% w/v SDS (Sequanal grade; Pierce, Rockford, Ill.), 36% glycerol, 5% β-mercaptoethanol, 0.01% bromophenol blue). Membranes were also probed with an antibody against tubulin (DM1a; Sigma) to demonstrate the presence of microtubules in the pellet samples.

Tau Polymerization.

Tau polymerization was induced using AA according to known methods (King, et al. (1999) Biochemistry 38:14851-14859), except that KCl was substituted for NaCl in the polymerization buffer. This substitution did not prevent filament formation. Briefly, tau protein (4 μM) was incubated at room temperature in reaction buffer (50 mM HEPES, pH 7.6, 50 mM KCl, 5 mM DTT) in the presence of 75 μM AA (in ethanol vehicle). Samples of soluble tau were prepared for perfusion in the same manner, except that arachidonic acid was excluded from the polymerization buffer. Control mixtures containing AA but lacking tau were prepared in parallel. Final ethanol concentration in all samples was 3.8%.

Electron Microscopy.

Polymerization reactions were allowed to proceed for 6 hours, fixed with 2% glutaraldehyde, spotted onto 300 mesh formvar/carbon-coated copper grids (Electron Microscopy Sciences, Hatfield, Pa.), and negatively stained with 2% uranyl acetate (King, et al. (1999) supra). Samples were examined with a JEOL JEM-1220 electron microscope at 60 kV and ×12,000 magnification, and photographs were taken with a MegaScan 794/20 digital camera and DigitalMicrograph software version 3.9.3 (Gatan, Pleasanton, Calif.).

In Vitro Phosphorylation of Tau by Fyn Kinase.

Wild-type tau, AT8 tau, or Δ144-273 tau (1 µM each) were incubated in phosphorylation buffer (5 mM HEPES, 125 mM NaCl, 0.05 mM EGTA, 25 mM Tris-HCl, 5 mM $MgCl_2$, 0.5 mM DTT, 0.005% BRIJ35; pH 7.4) supplemented with 1 mM ATP and containing active fyn kinase (0.055 U/µM tau). Phosphorylation was carried out at 32° C. for 50 minutes. Samples were diluted 1:1 in 2× Laemmli buffer at 0, 10, 20, 40, and 60 minutes to stop the reaction. Samples were stored at −20° C. until used for immunoblotting.

Squid Axoplasm Motility Assays.

Axoplasm from squid giant axons (Loligo pealii; Marine Biological Laboratory, Woods Hole, Mass.) was extruded according to known methods (Brady, et al. (1985) Cell Motil. 5:81-101). All proteins and inhibitors were diluted in ATP-supplemented X/2 buffer (175 mM potassium aspartate, 65 mM taurine, 35 mM betaine, 25 mM glycine, 10 mM HEPES, 6.5 mM $MgCl_2$, 5 mM EGTA, 1.5 mM $CaCl_2$, 0.5 mM glucose, pH 7.2) for perfusion. For experiments involving tau and their controls, reaction mixtures (containing tau alone, tau and AA, and AA alone) were diluted 1:1 in ATP-supplemented X/2 buffer (final tau concentration 2 µM, when present). Motility was analyzed using a ZEISS AXIOMAT microscope equipped with a ×100, 1.3 N.A. objective and DIC optics. Organelle velocities were measured by matching calibrated cursor movements to the speed of vesicles moving in the axoplasm (Morfini, et al. (2006) Nat. Neurosci. 9:907-916).

Purification of Membrane Vesicle Fractions from Squid Axoplasms.

Two "sister" axoplasms were prepared from the same animal and incubated with the appropriate effectors (control buffer, active GSK-3β monomeric tau, or filamentous tau) as for motility assays in X/2 buffer plus 1 mM ATP in 25 µl final volume. Active GSK-3p was from Sigma. After 40 minutes of incubation, axoplasms were transferred, along with perfusion buffer, to low protein binding 1.5 ml centrifuge tubes containing 200 µl of homogenization buffer (0.25 mM sucrose, 1 mM EDTA, 10 mM Hepes, pH 7.4, 1/100 protease inhibitor cocktail (Sigma), 1/200 phosphatase inhibitor cocktail set II (Calbiochem), 2 µM K252a (Calbiochem), 1 µM PKI (Upstate, Lake Placid, N.Y.)), and carefully homogenized by two passages through a 23-G syringe needle and five passages through a 27-G syringe needle using a 1-ml Hamilton pipette. Axoplasm homogenates were adjusted to 30% iodixanol by mixing 200 µl of axoplasm homogenates with 300 µl of solution D (50% (w/v) iodixanol, 10 mM $MgCl_2$ in 250 mM sucrose). A 500-µl layer of solution E (25% (w/v) iodixanol, 10 mM $MgCl_2$ in 250 mM sucrose) and a 100-µl layer of solution F (5% (w/v) iodixanol, 10 mM $MgCl_2$ in 250 mM sucrose) were loaded on top of the axoplasm homogenates. Samples were centrifuged at 250,000 g max for 1 hour at 4° C. in an RP55-S SORVALL rotor. Three hundred microliters containing floating vesicles were collected from immediately below the 5% iodixanol interface, and 60 µl of 6× loading sample buffer was added. In separate experiments, 0.1% TRITON X-100 was added to the axoplasm homogenates prior to centrifugation to confirm the membranous nature of this fraction. Immunoblots were developed using antibodies against kinesin-1 heavy chain (H2; Morfini, et al. (2007) supra), dynein intermediate chain (rabbit polyclonal V3), and SNAP-25 (Synaptic Systems). Quantitative immunoblotting was performed according to known methods (Morfini, et al. (2006) supra).

Statistical Analysis.

All experiments were repeated at least three times. Unless otherwise stated, the data were analyzed by ANOVA followed by post hoc Student-Newman-Keul's test in order to make all possible comparisons. Comparison of transport data from axoplasm under different conditions was done using a two-sample t-test of µ1-ρ2 with Datadesk statistical software (Data Description, Inc., Ithaca, N.Y.).

Where indicated, wild-type tau monomer group was used as the control group since no changes in motility rates are observed in this group compared to unperfused axoplasms. A two-way repeated measure ANOVA was used to analyze the immunoblotting results. When overall significance was reached, the Student-Newman-Keuls post-hoc analysis was used to make all possible comparisons. Significance was set at $p<0.01$ or $p<0.05$ as indicated. Data were expressed as mean±SEM, and significance was assessed at P values as noted. Sigmastat software (Systat Software, Inc., San Jose, Calif.) was used for statistical tests.

Example 2: Tau Amino Terminus Inhibits Kinesin-Dependent Axonal Transport

To evaluate the effect of tau on microtubule-dependent FAT, vesicle motility assays were used in isolated squid axoplasm. In this experimental system, the bidirectional transport of membrane-bound organelles (MBOs) can be directly observed by video-enhanced differential interference contrast (DIC) microscopy. This preparation preserves the ionic strength and complex environment of the cell, and, because the axoplasm is isolated from the cell body, nuclear effects can be ignored (Brady, et al. (1985) supra). Also, the absence of plasma membrane in this preparation allows for the introduction of experimental agents at tightly controlled concentrations (Morfini, et al. (2007) supra). This system was instrumental in the original discovery of kinesin-1 (Brady (1985) Nature 317:73-75), novel regulatory pathways for FAT (Morfini, et al. (2002) EMBO J. 21:281-293; Morfini, et al. (2004) EMBO J. 23:2235-2245; Morfini, et al. (2006) supra), and axonal-specific phosphorylation events (Grant, et al. (1999) J. Neurobiol. 40:89-102).

Monomeric hTau40 Binds to Squid Microtubules but does not Affect FAT.

Alternative splicing produces six major tau isoforms in the adult human central nervous system. Monomeric tau constructs derived from the shortest tau isoform (352 amino acid residues, hTau23) were produced using recombinant expression methods and their effects on FAT evaluated (Morfini, et al. (2007) supra). In the instant analysis, the longest isoform (441 amino acid residues, hTau40) was also used because of its greater propensity to form filaments (Gamblin, et al. (2003) supra). Unlike hTau23, hTau40 contains two alternatively spliced N-terminal exons (E2 and E3) and four microtubule binding repeats (R1-R4).

It has been demonstrated that monomeric hTau23 binds to axonal squid microtubules (Morfini, et al. (2007) supra). To rule out species-related artifacts, the ability of monomeric hTau40 to interact with endogenous squid microtubules was assayed. Microtubule-enriched fractions from squid optic lobe were prepared in the presence or absence of hTau40. After taxol-induced microtubule assembly, microtubules and associated proteins were sedimented by centrifugation and the resulting fractions (supernatants and microtubule-enriched pellets) probed with anti-tau antibodies. A tau construct with low binding affinity for microtubules (K23) was assayed in parallel to control for non-specific sedimentation. This analysis indicated that most K23 remained in the supernatant fraction. In contrast, hTau40 was depleted from the supernatant fraction and found in association with the microtubule-enriched pellet fraction, indicating that monomeric hTau40 can bind to endogenous squid microtubules.

Microtubule rigidity is increased when tau binds to the microtubule surface, and this effect is observable even at low, nonsaturating tau concentrations (Feigner, et al. (1997) *J. Cell Biol.* 138:1067-1075; Morfini, et al. (2007) supra). As an additional indicator of hTau40's ability to interact with squid microtubules, axoplasm was perfused with tau and the morphology of microtubules at the axoplasm periphery was examined. In the absence of exogenous tau, many of these microtubules exhibited a curved appearance. However, perfusion of monomeric hTau40 (2 µM) caused peripheral microtubules to acquire a straight, rigid appearance, consistent with binding of hTau40 to the microtubule surface (Morfini, et al. (2007) supra). Together with the sedimentation assay, these results demonstrate that hTau40 is capable of binding to squid microtubules.

The effects of monomeric hTau40 on FAT were subsequently examined. Axoplasm was perfused with monomeric, soluble hTau40 at 2 µM, which is within the physiological range for neurons (2-5 µM; Drubin, et al. (1985) *J. Cell Biol.* 101:1799-1807). The concentration of tubulin in squid axoplasm is 50 µM (Morris & Lasek (1984) *J. Cell Biol.* 98:2064-2076), resulting in a tau to tubulin ratio of approximately 1:25. FAT rates measured between 30 and 50 min post-perfusion were pooled and compared with axoplasms perfused with control buffer alone. As observed for other monomeric tau constructs (Morfini, et al. (2007) supra), perfusion of hTau40 at 2 µM showed no effect on either anterograde or retrograde FAT, demonstrating that physiological levels of monomeric hTau40 do not impair FAT in this system. Levels of monomeric tau constructs as great as 25 µM similarly had not effect on FAT (Morfini, et al. (2007) supra). Pulse-chase studies in mice overexpressing human tau at four times endogenous levels confirmed these observations (Yuan et al. (2008) supra).

Perfusion of Filamentous Tau Selectively Inhibits Anterograde FAT.

Recombinant hTau40 forms filaments in vitro when incubated with AA (Gamblin, et al. (2003) supra), and these filaments are morphologically similar to those isolated from AD neuronal tissue (King, et al. (1999) supra). To determine the effects of filamentous tau on FAT, hTau40 filaments (2 µM) were perfused into squid axoplasm and anterograde and retrograde FAT rates were monitored. Unlike monomeric tau, hTau40 filaments inhibited anterograde, kinesin-dependent FAT rates (P=0.001) when perfused at the same concentration as monomeric hTau40 (2 µM). Perfusion of axoplasms with polymerization buffer alone had no effect on FAT, demonstrating that the effects on FAT were due to the presence of filamentous tau. Significantly, retrograde FAT rates remained unaffected, indicating that the effects of hTau40 filaments on anterograde FAT were not due to alterations in microtubule integrity or steric effects due to binding of tau to microtubules. Supporting this idea, htau40 filaments (2 µM) did not produce changes in microtubule morphology when perfused into axoplasm, which also indicates that filamentous tau does not bind to microtubules. Similarly, perfusion of equivalent amounts of polymerization buffer (containing AA but no tau) had no effect on FAT.

The Effect of Tau Filaments on FAT Depends on the Extreme N-Terminus of Tau.

Several studies suggest important functional roles for both the amino and carboxy termini of tau (Brandt, et al. (1995) *J. Cell Biol.* 131:1327-1340; Amadoro, et al. (2004) *Cell Death Differ.* 11:217-230; Amadoro, et al. (2006) *Proc. Natl. Acad. Sci. USA* 103:2892-2897; Lee (2005) *Biochim. Biophys. Acta* 1739:323-330), and the study of selected modifications of these domains constitutes an emerging area of interest in AD (Gamblin, et al. (2003) supra; Guillozet-Bongaarts, et al. (2005) *Neurobiol. Aging* 26:1015-1022). To determine whether these domains are involved in FAT inhibition, two tau constructs were assayed, Δ2-18 and 1-421, containing deletions at the extreme amino- and carboxy-termini, respectively. These deletions do not prevent tau from forming filaments (Berry, et al. (2003) *Biochemistry* 42:8325-8331; Gamblin, et al. (2003) supra). However, the buffer conditions required for axoplasm perfusion differ from the buffer conditions used in previous tau assembly assays. Therefore, the formation of tau filaments under these experimental conditions was assessed by electron microscopic analysis. The results of this analysis indicated that hTau40, Δ2-18, and 1-421 all form morphologically indistinguishable filaments under these buffer conditions.

The effects of Δ2-18 and 1-421 filaments on FAT were subsequently evaluated. Axoplasms perfused with monomeric hTau40 (2 µM) were used as an experimental control, because this treatment results in FAT rates that are indistinguishable from control buffer alone. Filaments composed of hTau40 (hTau40 F) and 1-421 (1-421 F) significantly reduced anterograde FAT rates, compared with hTau40 monomer (hTau40 M; *P=0.0001 by a two-sample t-test). In contrast, Δ2-18 filaments (Δ2-18 F) had no effect on FAT. Retrograde transport was unaffected in all conditions. These results indicate that the first 18 amino acid residues of tau are necessary for the inhibitory effect of tau filaments on anterograde FAT. Although the magnitude of the 1-421 filament effect was not as great as that of hTau40 filaments in the time period under analysis, the pattern of inhibition was similar and the effect of 1-421 filaments was not significantly different from that of full-length hTau40 filaments in a t-test. It remains to be determined whether the apparent difference is the result of variability in the effective concentration of the two types of filaments or whether some small difference in the structure of the 1-421 filaments affects the presentation of the N-terminus.

Monomeric Tau Constructs Lacking the C-Terminal Half of the Protein Recapitulate the Effects of Tau Filaments on FAT.

Results from deletion experiments indicated that the first 18 amino acid residues at the amino terminus of tau are required to elicit the inhibitory effect of tau filaments on FAT. However, various full-length tau constructs including the amino terminal 18 amino acid residue domain do not affect FAT when perfused in monomeric, soluble form (Morfini, et al. (2007) supra), suggesting this domain could be abnormally exposed in the context of filamentous hTau40. Biochemical studies identified an intramolecular interaction between the amino and C termini of monomeric tau constructs (Horowitz, et al. (2004) *J. Neurosci.* 24:7895-7902; Jeganathan, et al. (2006) *Biochemistry* 45:2283-2293). Therefore, the effect of endogenous tau isoforms lacking the C-terminal half of the protein on FAT was evaluated. These isoforms, Tau6P and Tau6D, are the products of two cryptic splice sites in exon 6. They are identical to canonical tau from residues 1-144, at which point splicing introduces a unique 11-amino acid residue sequence followed by a stop codon. The specific 11 amino acid residues differ depending on whether the splice site is proximal or distal to the beginning of exon 6 (Luo, et al. (2004) supra). Tau6P and Tau6D terminate prior to the MTBR region and so are not expected to interact with microtubules (Lee, et al. (1989) *Neuron* 2:1615-1624) or to form filaments (Abraha, et al. (2000) supra; von Bergen, et al. (2000) *Proc. Natl. Acad. Sci. USA* 97:5129-5134). When axoplasm was perfused with monomeric Tau6P or Tau6D (2 μM), anterograde FAT was inhibited (P=0.0001), but retrograde transport remained unchanged. Because the effects of these two isoforms were indistinguishable, data from Tau6P and Tau6D were pooled. The inhibitory effect of these tau isoforms was indistinguishable from that of hTau40 filaments, indicating that the amino terminus of tau is sufficient to trigger FAT inhibition.

The Effects of Tau Filaments on FAT are Mediated by GSK-3 Activity.

The effect of tau filaments and monomeric 6P/6D tau isoforms on anterograde FAT indicated that the effect was unlikely to be due to steric hindrance of kinesin by tau at the microtubule surface, because filamentous tau is not expected to bind to microtubules and Tau6P/6D isoforms lack an MTBR domain. Instead, it was contemplated that FAT inhibition might occur through a signaling pathway that regulates the activity of conventional kinesin, the major anterograde motor in this isolated axoplasm system.

Several axonal kinases have been identified that play a role in regulating conventional kinesin-dependent FAT, including JNK (Morfini, et al. (2006) supra), and GSK-3 (Morfini, et al. (2002) supra) kinases, among others (Morfini et al. (2009) *J. Neurosci.* 29(41):12776-86). JNK3 phosphorylates kinesin heavy chains (KHCs), which inhibits conventional kinesin binding to microtubules and results in reduced anterograde FAT (Morfini, et al. (2006) supra). The effects of abnormal JNK activation can be blocked by SB203580 (Morfini, et al. (2006) supra), a pharmacological inhibitor that acts on JNK2/3 and other members of the stress-activated protein kinase (SAPK)/JNK family (Coffey, et al. (2002) *J. Neurosci.* 22:4335-4345; Morfini, et al. (2006) supra). To determine whether tau filaments inhibit anterograde FAT through a mechanism involving JNK activation, tau filaments were coperfused with SB203580 (5 μM). Coperfusion of tau filaments with SB203580 did not block the effect of tau filaments on FAT (different from soluble tau at P=0.001), indicating that this effect was independent of JNK and other SAPK/JNK kinases (i.e., p38s).

To evaluate whether tau filaments inhibit anterograde FAT through a mechanism involving GSK-3 activation, hTau40 filaments (2 μM) we coperfused with cAMP response element-binding protein phosphopeptide (CREBpp; 0.5 mM). Although many kinases phosphorylate intact CREB protein, the peptide fragment employed here (KRREILSRRPpSYR; SEQ ID NO:8) is selectively phosphorylated by GSK-3 and therefore acts as a competitive inhibitor of other GSK-3 substrates (Wang, et al. (1994) *Anal. Biochem.* 220:397-402). Perfusion of CREBpp in squid axoplasm alone has no effect on FAT, although it effectively blocks the effects of active GSK-3 on kinesin-1-based motility (Morfini, et al. (2002) supra; Morfini, et al. (2004) supra). Remarkably, coperfusion of tau filaments and CREBpp blocked tau filament-induced effects on FAT, indicating that the effects of the filaments are dependent on GSK-3 activation. CREBpp also blocked the effects of 1-421 tau filaments, indicating that these filaments act through the same mechanism as filaments composed of full-length hTau40.

To confirm that GSK-3 activity was required for tau filaments to inhibit kinesin-dependent FAT, tau filaments were coperfused with the lithium mimetic ING-135 (100 nM), a highly specific pharmacological inhibitor of GSK-3 (Kozikowski, et al. (2007) supra). As with CREBpp, coperfusion with ING-135 blocked the effect of tau filaments, and perfusion of ING-135 alone had no effect on FAT. Together, these results indicate that the effect of tau filaments on anterograde FAT involves activation of axonal GSK-3.

Phosphorylation of kinesin light chains (KLCs) by GSK-3 triggers the chaperone-dependent dissociation of kinesin-1 from its cargo (Morfini, et al. (2002) supra; Pigino, et al. (2003) *J. Neurosci.* 23:4499-4508). To determine whether tau filaments induce the dissociation of kinesin-1 from cargo, "sister" axoplasms were obtained from individual animals and treated with monomeric or filamentous hTau40 (2 μM). For comparison, other axoplasm pairs were treated with control buffer or with recombinant, active GSK-3β. After 40 minutes of incubation, axoplasmic vesicle fractions were isolated and kinesin-1 levels were evaluated with an antibody against KHCs. Antibodies recognizing the synaptic integral membrane protein SNAP-25 served as a control for equal vesicle protein loading. The recovery of SNAP-25, kinesin-1, and dynein from axoplasmic vesicles was blocked by addition of 0.1% TRITON X-100 to axoplasm homogenates prior to centrifugation, confirming the membranous nature of this fraction. Perfusion of either filamentous tau or active GSK-3β resulted in an ~50% decrease in the amount of kinesin-1 associated with vesicles relative to monomeric tau or control buffer, respectively (P=0.05 for filamentous tau). In contrast, levels of dynein intermediate chain were unaffected. These results demonstrated that both tau filaments and active GSK-3 selectively inhibited anterograde FAT by promoting dissociation of conventional kinesin, but not dynein, from its transported vesicular cargo.

PP1 Activity Mediates the Inhibitory Effect of Tau Filaments on FAT.

GSK-3 is inactive when phosphorylated (Wang, et al. (1994) *J. Biol. Chem.* 269:14566-14574) and can be activated by axonal phosphatases (Wang, et al. (1994) supra; Morfini, et al. (2004) supra). Therefore, it was determined whether the inhibitory effects of tau filaments involve the activity of axoplasmic phosphatases. To this end, axoplasm was coperfused with tau filaments and okadaic acid (100 nM). Okadaic acid inhibits two major serine-threonine phosphatases, namely, protein phosphatase (PP1) and protein phosphatase 2A (PP2A). Concentrations of okadaic acid alone up to 1 μM have no effect on FAT (Bloom, et al. (1993) *J. Cell Biol.* 120:467-476). Remarkably, okadaic acid blocked the effect of tau filaments on FAT, indicating that tau filament-mediated inhibition of anterograde FAT involved the activity of a major serine-threonine phosphatase. To distinguish between PP1 and PP2A activity, filaments were coperfused with 50 nM inhibitor-2 (1-2). 1-2 selectively inhibits PP1, but has no effect on PP2A, even at micromolar concentrations (Cohen (1991) *Methods Enzymol.* 201:389-398). When coperfused with tau filaments, 1-2 prevented FAT inhibition, indicating that axonal PP1 activity mediates the effect of tau filaments on FAT.

These results provide a novel link between tau aggregation and neuronal dysfunction and identify a specific gain-of-function mechanism conferred by the aggregation process. Furthermore, these studies indicate that inhibition of kinesin-1-based motility represents an important pathogenic event in AD and other tauopathies.

Example 3: Tau Conformation Determines Whether Tau Inhibits Anterograde Fast Axonal Transport 6D and 6P Tau Isoforms Inhibit Anterograde FAT. As demonstrated herein, tau filaments specifically inhibit anterograde FAT in the squid axoplasm through N-terminal mediated mechanisms involving PP1, GSK, and dissociation of the cargo from kinesin-1. 6D and 6P tau represent naturally occurring isoforms expressed in some tissues and may have biological relevance (Andreadis (2005) *Biochim. Biophys. Acta* 1739(2-3):91-103). They are produced by one of two cryptic splice sites within exon 6 of tau, one proximal to the cannonical site (6P) and one distal (6D). The carboxy end of each isoform terminates in unique 11 amino acid stretches not present in canonical tau. To further analyze the role of the N-terminal isoforms of tau, vesicle motility assays in isolated axoplasm were conducted. The results of this analysis indicated that full-length wild-type tau monomers (2 μM) had no effect on axonal transport in squid axoplasm. When added to isolated squid axoplasm, 6D tau monomers (2 μM) significantly inhibited anterograde FAT compared to wild-type tau monomer, but no effect was observed in retrograde transport. Similarly, 6P tau monomers (2 μM) specifically inhibited anterograde FAT, and had no effect on retrograde transport. Since similar levels of inhibition were obtained with 6D and 6P constructs, which are identical in the first 143 amino acids, the 6D tau construct was further analyzed.

6D Tau Inhibits FAT via a PP1-GSK3 Signaling Cascade.

In order to determine whether 6D inhibits anterograde FAT via the same signaling cascade as filamentous full-length tau, PP1 and GSK3 were inhibited in squid axoplasms challenged with 6D tau. Co-perfusion of 6D tau with 1-2 (50 nM), a specific PP1 inhibitor, resulted in complete prevention of anterograde FAT inhibition. Similarly, addition of okadaic acid (OK; 200 nM), a non-specific PP1/PP2 inhibitor, also abolished anterograde FAT inhibition by 6D tau. The same effect was noted when 6P tau and OK were co-perfused. Co-perfusion of 6D tau and ING-135 (100 nM), a specific GSK3 inhibitor, completely blocked 6D-mediated anterograde FAT inhibition. 6D tau significantly inhibited anterograde FAT when compared to wild-type tau monomers, 6D+1-2, and 6D+ING-135 groups. Retrograde transport was not affected by any 6D tau group when compared to wild-type tau, but a significant difference was detected between the 6D tau and 6D+ING-135 groups. Together, these data demonstrate that 6P and 6D isoforms of tau inhibit anterograde FAT by activating PP1 and GSK3, which leads to a dissociation of cargo from kinesin-1 (Morfini, et al. (2007) supra), which is the same mechanism used by full-length tau filaments.

Amino Acids 2-18 are Necessary and Sufficient for Anterograde FAT Inhibition.

As described in Example 2, filaments composed of tau with amino acids 2-18 deleted from the N-terminus (Δ2-18) do not inhibit anterograde FAT, indicating that this domain is a necessary part of the inhibition cascade. To determine whether the domain was responsible for this activity in the amino isoforms, squid axoplasms were perfused with Δ2-18 6D tau (2 μM). As was found with Δ2-18 tau filaments, monomeric Δ2-18 6D had no effect on axonal transport demonstrating that amino acids 2-18 are necessary for 6D-mediated anterograde FAT inhibition.

Therefore, it was subsequently determined whether amino acids 2-18 were sufficient to induce anterograde FAT inhibition or whether this effect required the surrounding amino acids at the amino end of the tau molecule. Intact axoplasms were perfused with 2 μM of a synthetic peptide composed of amino acids 2-18 or with a scrambled control peptide at the same concentration. The 2-18 peptide induced a significant inhibition of anterograde FAT, while its scrambled version failed to cause any inhibition. Retrograde transport was unaffected in all conditions. Together, these data demonstrate that amino acids 2-18 in the N-terminal region of tau are both necessary and sufficient to induce FAT inhibition.

The "PAD" Peptide Inhibits FAT Via a PP1-GSK3 Signaling Cascade.

PP1 and GSK3 were inhibited to establish whether FAT inhibition induced by the 2-18 peptide resulted from an activation of the PP1-GSK3 signaling cascade in the same fashion as 6D tau and filamentous full-length tau. Co-perfusion of the 2-18 peptide with 1-2 (50 nM) or ING-135 (100 nM) completely prevented anterograde FAT inhibition. It is important to note that none of the 2-18 peptide+inhibitor groups were different from the wild-type tau monomer group, and retrograde transport was not affected by any treatment. These data demonstrate that amino acids 2-18 in tau are both necessary and sufficient to activate the PP1-GSK-cargo dissociation cascade. This domain in the tau molecule is herein referred to as the "phosphatase-activating domain" (PAD) of tau.

Disease-Associated Changes in Tau Cause Inhibition of FAT.

The "paperclip" conformation in tau or yet undefined, but similar conformations, likely play an important role in determining whether tau monomers affect axonal transport. The "paperclip" conformation involves an interaction of the C-terminus with the MTBR and the N-terminus with the C-terminus. In this conformation, the PAD in the N-terminus may be blocked from initiating the PP1-GSK3 cascade. Exposure of the N-terminus of tau, whether through aggregation of full-length wild-type tau, truncated N-terminal isoforms, or simply the PAD peptide, initiates the PP1-GSK3 signaling cascade leading to inhibition of anterograde FAT. These data indicated that disease-related modifications to tau that expose the PAD would cause anterograde FAT inhibition.

It has been demonstrated that pseudophosphorylation at S199, S202 and T205 in tau (to mimic the AT8 epitope) promotes extension of the N-terminus out of the "paperclip" conformation. Thus, phosphorylation at these sites would generate tau in which exposure of the PAD in the N-terminus is increased. To determine whether soluble, AT8-phosphorylated tau could inhibit anterograde FAT, soluble monomers of S199E/S202E/T205E tau were perfused into isolated squid axoplasms. Indeed, AT8 tau significantly reduced the rate of anterograde FAT, while retrograde transport was unaffected. These data indicate that phosphorylation of tau within this region, which is associated with hyperphosphorylation of tau in AD, produces soluble monomeric tau capable of inhibiting anterograde FAT.

A mutation in the tau gene, which is associated with a case of FTDP-17 that results in deletion of amino acids 144-273 (Δ144-273 tau), has been identified (Rovelet-Lecrux, et al. (2009) *Hum. Mutat.* 30(4):E591-602). This mutation would generate tau in which the PAD of the N-terminus is constitutively exposed because the deleted portion of tau plays a pivotal role in folding of the N-terminus. To determine whether this mutant form of tau has an effect on axonal transport, isolated squid axoplasms were perfused with Δ144-273 tau. The results of this analysis indicated that Δ144-273 tau significantly inhibited the rate of anterograde FAT, while retrograde transport was unaffected. Taken together, these data indicate that disease-associated tau mutations that lead to increased exposure of the PAD in the N-terminus may be toxic to axonal transport.

Fyn-Mediated Phosphorylation of Y18 is Reduced in Disease-Associated Tau Species.

Fyn kinase is a non-receptor tyrosine kinase known to phosphorylate tau at Tyr18 and phosphoTyr18 (pTyr18) and is found in tau inclusions of AD brains (Lee, et al. (2004) supra). Phosphorylation at Tyr18 by fyn kinase prevents tau-mediated inhibition of anterograde FAT in squid axoplasm. To determine whether the fyn-derived phosphorylation of Tyr18 is affected by AT8 pseudophosphorylation or deletion of amino acids 144-273, the AT8 tau and Δ144-273 tau were incubated with fyn kinase in vitro. When compared to wild-type tau, AT8 tau and Δ144-273 tau had a slower rate and lower maximal level of phosphorylation at Tyr18. These data indicate that a mechanism capable of preventing tau's inhibition of anterograde transport (e.g., phosphorylation at Tyr18 by fyn kinase) is impaired for AT8 tau or Δ144-273 tau, which are associated with AD and FTDP-17, respectively.

Example 4: Tau Peptide Binding Agent Prevents Tau-Mediated Inhibition of FAT

Using conventional immunological methods, antibodies to the PAD peptide were generated. One of these antibodies, designated TNT1, was analyzed for its ability to detect pathogenic forms of tau. Protein extracts from control (normal) and AD human brain were prepared, separated by SDS-PAGE and immunoblots were probed with the TNT1 antibody. This analysis indicated that the TNT1 antibody could bind denatured tau in both control and AD brain fractions. Furthermore, the antibody bound to tau in both soluble and PHF (paired helical filaments) fractions of AD brains.

Dot blots with TNT1 and Tau12 antibodies showed that these antibodies reacted with tau in Sarkosyl soluble and Sarkosyl insoluble (PHF tau) fractions from age-matched control and AD brains. Tau12 is a mouse monoclonal antibody specific for residues 9-18 in the amino terminus of tau (Horowitz, et al. (2004) *J. Neurosci.* 24(36):7895-902) and was shown to bind tau in both control and AD brains.

Most tau in control brains was in the Sarkosyl soluble fraction. Under nondenaturing conditions, TNT1 bound to little or no tau in either soluble fractions, while Tau12 showed that tau was present. The tau epitope for TNT1 appeared to be sequestered in the control samples. In contrast, TNT1 immunoreactivity was strong in both soluble and insoluble fractions from AD brains.

Immunohistochemical analysis was also conducted and showed that TNT1 immunoreactivity was low in sections of the enthorhinal cortex and hippocampus CA1 regions of the control brain, but was extensive in the corresponding sections from AD brains. At higher magnification, TNT1 immunoreactivity was apparent in cell bodies, proximal dendrites, neuropil, and in neurites associated with plaques. In age-matched control brains, AT8 (anti-PHF-tau antibody) and TNT1 immunoreactivity was sparse and largely colocalized. AT8 recognizes a phosphorylated epitope in tau that is diagnostic of AD pathology and this distribution is consistent with the published reports of low levels of AT8 immunoreactivity in aging brain. In contrast, in sections from patients with mild AD or mild cognitive impairment, both AT8 and TNT1 immunoreactivities were significantly increased, but TNT1 was more extensive. The AT8 immunoreactivity was consistent with literature showing increased AD pathology in patients at this stage. In sections from patients with severe AD, AT8 and TNT1 immunoreactivity was extensive and severe. As in less severe cases, there was extensive colocalization of AT8 and TNT1 immunoreactivity. These data therefore demonstrate that TNT1 binds to pathogenic tau in AD brain.

Figure 1B:
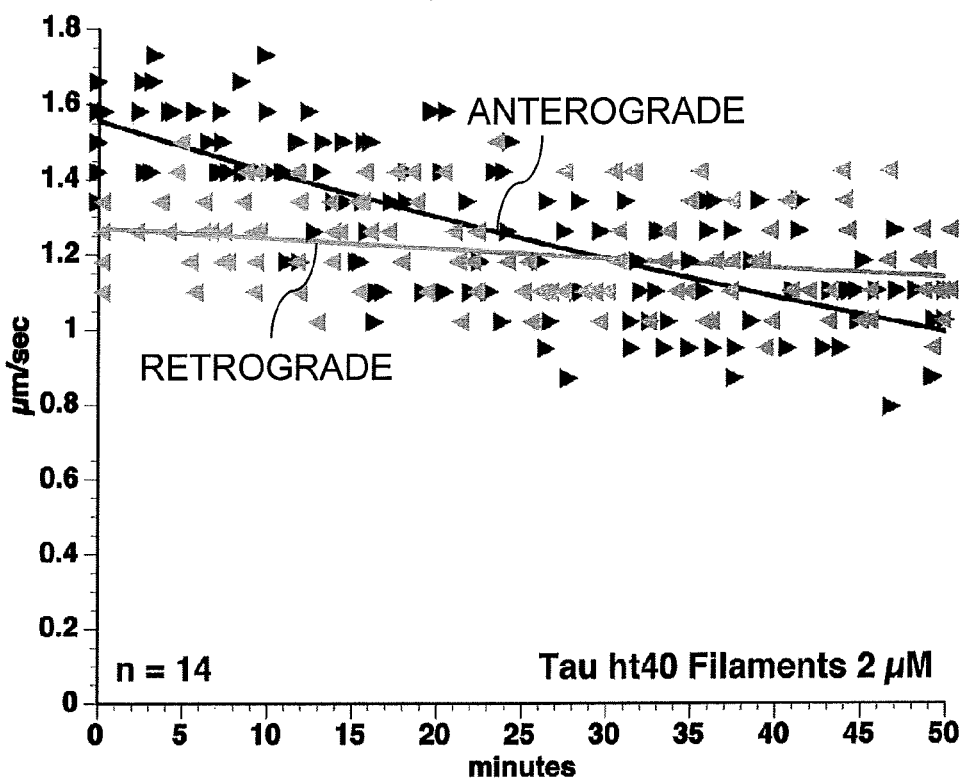

To determine whether the TNT1 antibody could block the activity of pathogenic tau, FAT studies were conducted. The results of this analysis indicated the coperfusion of Tau filaments and TNT1 completely blocked the inhibition of anterograde FAT by tau filaments (FIG. 1). Accordingly, TNT1 is of use as a blocking antibody that inhibits the activity of pathogenic tau.

What is claimed is:

1. An isolated monoclonal antibody, or antigen binding antibody fragment thereof, raised against a tau peptide consisting of SEQ ID NO:1 or a peptide fragment thereof, wherein said antibody or antigen binding antibody fragment binds the tau peptide consisting of SEQ ID NO:1 and does not bind wild-type, non-denatured, soluble tau monomer.

2. The isolated antibody or antigen binding antibody fragment of claim 1, wherein the tau peptide or peptide fragment is not post-translationally modified.

3. The isolated antibody or antigen binding antibody fragment of claim 1, wherein the peptide fragment is between 5 and 16 amino acid residues in length.

4. The isolated antibody or antigen binding antibody fragment of claim 1, wherein the antibody or antigen binding antibody fragment:
   (a) binds tau paired helical filaments,
   (b) binds denatured tau, or
   (c) binds pathogenic tau from the brain of a patient with Alzheimer's disease.

5. A pharmaceutical composition comprising the isolated antibody or antigen binding antibody fragment of claim 1 and a pharmaceutically acceptable carrier.

6. A method for treating a tauopathy comprising administering to a subject with a tauopathy the pharmaceutical composition of claim 5 thereby treating the subject's tauopathy.

7. The method of claim 6, wherein the tauopathy comprises Alzheimer's disease, progressive supranuclear palsy, frontotemporal dementia, Pick's disease, corticobasal degeneration, or post-encephalitic parkinsonism.

* * * * *

UNITED STATES PATENT AND TRADEMARK OFFICE
CERTIFICATE OF CORRECTION

PATENT NO. : 9,862,761 B2
APPLICATION NO. : 14/863997
DATED : January 9, 2018
INVENTOR(S) : Scott Thomas Brady et al.

Page 1 of 1

It is certified that error appears in the above-identified patent and that said Letters Patent is hereby corrected as shown below:

On the Title Page

At item (73), please delete:
"Trustes"

Please insert:
-- Trustees --

At Column 1, Line 16, please delete:
"This invention was made with government support under contract numbers NS049834 and AG14453 awarded by the National Institutes of Health and contract numbers NS23868, NS23320, NS41170, and NS43408 awarded by the National Institute of Neurological Disorders and Stroke. The government has certain rights in the invention."

Please insert:
-- This invention was made with government support under grant nos. NS023868, NS023220, NS041170, NS043408, NS049834 and AG009466 awarded by the National Institutes of Health. The government has certain rights in this invention. --

Signed and Sealed this
Twenty-sixth Day of November, 2019

Andrei Iancu
*Director of the United States Patent and Trademark Office*